United States Patent [19]

Gittos et al.

[11] Patent Number: 4,704,389

[45] Date of Patent: Nov. 3, 1987

[54] AROMATIC OMEGA-ALKYL-IMINO-TETRAHYDRO-6H-1,3-THIAZIN-6-ONE DERIVATIVES

[75] Inventors: Maurice W. Gittos, Plobsheim; Marcel Hibert, Strasbourg, both of France

[73] Assignee: Merrell Dow Pharmaceuticals Inc., Cincinnati, Ohio

[21] Appl. No.: 5,291

[22] Filed: Jan. 16, 1987

Related U.S. Application Data

[63] Continuation of Ser. No. 836,275, Mar. 5, 1986, abandoned.

[51] Int. Cl.$^4$ .................... A61K 31/54; C07D 407/12; C07D 417/12
[52] U.S. Cl. ..................................... 514/226; 544/54; 544/6
[58] Field of Search ....................... 514/226; 544/54, 6

[56] References Cited

U.S. PATENT DOCUMENTS

4,250,173  2/1981  Cantello ................................ 544/54
4,311,838  1/1982  Davis et al. .......................... 544/54

FOREIGN PATENT DOCUMENTS

170213  2/1986  European Pat. Off. .

OTHER PUBLICATIONS

Peroutka, Biol. Psychiatry, vol. 20, pp. 971–979 (1985).

*Primary Examiner*—John M. Ford
*Attorney, Agent, or Firm*—Stephen L. Nesbitt

[57] ABSTRACT

This invention relates to aromatic ω-alkylimino-tetrahydro-6H-1,3-thiazine-6-one derivatives, to a process for the preparation of same, and to their use as anxiolytic and antihypertensive agents.

8 Claims, No Drawings

AROMATIC OMEGA-ALKYL-IMINO-TETRAHYDRO-6H-1,3-THIAZIN-6-ONE DERIVATIVES

CROSS REFERENCE TO RELATED APPLICATION

This is a continuation of application Ser. No. 836,275, filed Mar. 5, 1986, now abandoned.

FIELD OF THE INVENTION

This invention relates to certain aromatic ω-alkyliminotetrahydro-6H-1,3-thiazin-6-one derivatives and their use as anxiolytic agents and as antihypertensive agents.

BACKGROUND OF THE INVENTION

Anxiety has been defined as an apprehension or concern regarding some future event. Most, if not all, people occasionally suffer some symptoms of anxiety in response to appropriate stimuli. In some individuals, these feelings of anxiety or panic in response to the everyday pressures of life can be overwhelming, rendering the individual an unproductive member of society. Whereas individual group counseling represents the preferred primary mode of therapy, the use of chemotherapeutic agents has proven to be a useful adjunct in the treatment of anxiety, thereby enabling a seriously afflicted individual to regain productive status while undergoing concurrent psychotherapy.

Compounds of the class of benzodiazepines are currently the therapeutic agents of choice in the treatment of anxiety. In particular, chlordiazepoxide, diazepam and oxazepam are commonly used. This class of compounds has a great potential for misuse, particularly among the class of patients undergoing therapy. Moreover, the benzodiazepines generally possess undesired sedative effects and process detracting interactions with other drugs, including for example, alcohol.

Applicants have now discovered a class of novel aromatic ω-alkylimino-tetrahydro-6H-1,3-thiazin-6-ones, which are useful as antianxiety agents, and which are generally free from the undesirable effects of the benzodiazepines. The compounds disclosed herein, when practiced in accordance with the teachings of this invention help to alleviate such symptoms as excessive fear, worry, restlessness, tension, stress, neurotic depression and are useful in the relief of some personality disorders. Additionally, certain compounds of this invention are useful antihypertensive agents which have the effect of lowering blood pressure in patients in need thereof.

SUMMARY OF THE INVENTION

This invention is directed to a class of aromatic ω-alkylimino-tetrahydro-6H-1,3-thiazin-6-ones having the formula

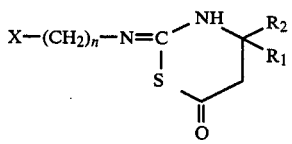
(1)

wherein n is an integer from 2 to 5; $R_1$ and $R_2$ are each methyl or when taken together form a tetramethylene or pentamethylene ring; X is the radical

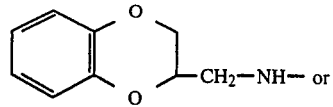

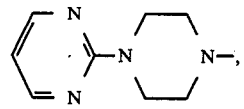

and the pharmaceutically acceptable acid addition salts thereof.

This invention also discloses a process for the preparation of said compounds, pharmaceutical compositions thereof, and to their use as anxiolytic agents. In addition, certain of these compounds are useful as antihypertensive agents.

DETAILED DESCRIPTION OF THE INVENTION

As used herein the term "pharmaceutically acceptable acid addition salts" is intended to apply to any non-toxic organic or inorganic acid addition salts of the base compounds represented by Formula I. Illustrative inorganic acids which form suitable salts include hydrochloric, hydrobromic, sulphuric and phosphoric acid and acid metal salts such as sodium monohydrogen orthophosphate and potassium hydrogen sulfate. Organic acids which form suitable salts include the mono, di and tricarboxylic acids. Illustrative examples of such acids include: acetic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicylic, 2-phenoxybenzoic acids, and sulfonic acids, such as methanesulfonic acid or 2-hydroxyethanesulfonic acid. Either the mono or the di-acid salts can be formed, when possible, and such salts can exist in either a hydrated or a substantially anhydrous form. In general, the acid addition salts of these compounds are crystalline materials which are soluble in water and in various hydrophilic organic solvents. In comparison to their free base forms, such salts generally demonstrate higher melting points and an increase in chemical stability.

As can be seen in formula (1) above, two specific subclasses of compounds fall within the scope of the present invention, which are illustrated as follows:

2-[ω-[(2,3-dihydro-1,4-benzodioxin-2-yl)methylamino]alkylimino]tetrahydro-6H—1,3-thiazin-6-ones

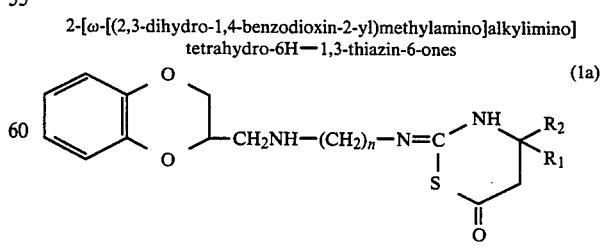
(1a)

and

2-[ω-[4-(2-pyrimidinyl)-1-piperazinyl]alkylimino]tetrahydro-6H—1,3-thiazin-6-ones

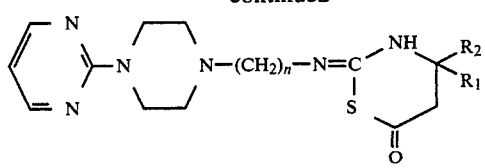

Compounds of formula (1a) represent the preferred class of compounds. Compounds of this class possess both anxiolytic and antihypertensive properties. Compounds of formula (1b), on the other hand, possess anxiolytic properties without antihypertensive properties.

The alkylene group depicted above, represented as $-(CH_2)_n-$, can be considered as a connecting bridge separating two terminal heterocyclic ring systems. As indicated above, the symbol n represents an integer of from 2 to 5. Those alkylene groups in which n represents from 2 to 4 carbon atoms, represent the preferred alkylene chain lengths.

The aromatic ω-alkylimino-tetrahydro-6H-1,3-thiazin-6-ones of formula (1) can be prepared in an analogous manner using standard techniques known to the art. Thus, such compounds can be prepared via the nucleophilic condensation of an alkyl ester of 3-isothiocyanopropionic acid (2) with an appropriate nucleophilic alkylamine of formula (3) to form an alkyl ester of 3-[(N-alkyl)thioureido]propionic acid (4) as shown below.

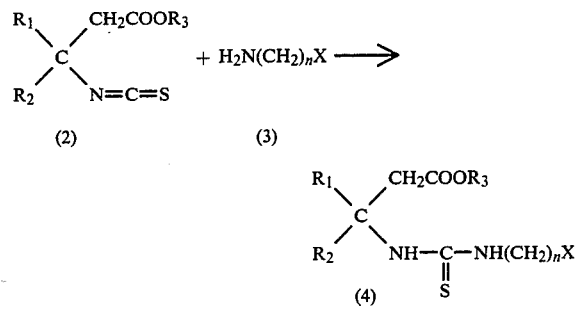

wherein n, $R_1$, $R_2$ and X are as previously defined and $R_3$ represents a lower alkyl group having from 1 to 4 carbon atoms. Illustrative lower alkyl groups include methyl, ethyl, propyl, isopropyl, butyl and sec-butyl.

The nucleophilic condensation is preferably conducted using equimolar amounts of the alkylamine (3) with the alkyl ester of 3-isothiocyanopropionic acid (2) for a period of from about 1 hour to 24 hours depending upon the particular reactants employed. The reaction temperature can range from about 25° C. to 140° C.; preferably the reaction is conducted at a temperature ranging from 40° C. to 125° C.

Inasmuch as the reactants employed are typically crystalline materials, the use of solvents is preferred. Suitable solvents include any non-reactive solvent, preferably an aprotic solvent which has a boiling point in the range of from 40° C. to 150° C. Solvents which can be suitably employed include solvents such as petroleum ethers; chlorinated hydrocarbons such as carbon tetrachloride, ethylene chloride, methylene chloride or chloroform; chlorinated aromatic compounds such as 1,2,4-trichlorobenzene, or o-dichlorobenzene; carbon disulfide; ethereal solvents such as diethylether, tetrahydrofuran or p-dioxane; or aromatic solvents, such as benzene, toluene or xylene. Especially preferred solvents are those which are known to promote nucleophilic reactions, such as dimethysulfoxide and dimethylformamide.

The 3-isothiocyanopropionic acid esters (2) can be prepared by reacting the alkyl esters of 3-aminopropionic acid (5) with carbon disulfide in the presence of a base such as sodium hydroxide or triethylamine using standard procedures. The alkyl esters of 3-[(N-alkyl)thioureido]propionic acid (4) are not isolated, since they spontaneously cyclize to the desired aromatic ω-alkylimino-tetrahydro-6H-1,3-thiazine-6-ones (1) of the present invention. This cyclization is enhanced by the presence of a catalytic quantity of a strong base, such as sodium or potassium tert-butoxide and is further enhanced at elevated temperatures ranging from 40° to 100° C.

The alkylamines of formula (3) wherein the symbol X represents the radical

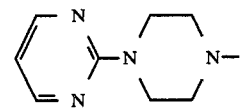

are known compounds, see U.S. Pat. No. 1,332,194.

Those alkylamines of formula (3) wherein the symbol X represents the 2-(2,3-dihydro-1,4-benzodioxin-2-yl)methylamino moiety can be prepared utilizing the corresponding 2-(2,3-dihydro-1,4-benzodioxin-2-yl)methylamine, which is a known compound. Schiff's base formation with benzaldehyde or a substituted benzaldehyde, such as p-methoxybenzaldehyde, followed by a catalytic reduction of the imino group utilizing hydrogen and a (Pd/C) catalyst, results in the formation of the corresponding benzylamine. Reaction of the benzylamine with chloroalkylnitrile in refluxing butanol, followed by a reduction of the nitrile function with lithium aluminum hydride or hydrazine and a Raney nickel catalyst forms the corresponding N-benzyl-4-(2,3-dihydro-1,4-benzodioxin-2-ylmethyl)-1,ω-diaminoalkane. Catalytic hydrogenolysis (Pd/C) of the benzyl or substituted benzyl group results in the formation of the desired 2-(2,3-dihydro-1,4-benzodioxin-2-ylmethyl)-1,ω-diaminoalkane (3).

Alternatively, the compounds of formula (1) can be prepared via the reaction of the known alkyl esters of 3-aminopropionic acid (5) with an alkylisothiocyanate which contains a suitable leaving group (6) to prepare alkyl ester derivatives of 3[(N-alkyl)thioureido]propionic acid (7). Reaction of (7) with an aromatic amine results in the formation of the alkyl esters of 3-[(N-alkyl)thioureido]propionic acid (4) which can then be cyclized to the compounds of formula (1) as previously described. This reaction scheme can be indicated as follows:

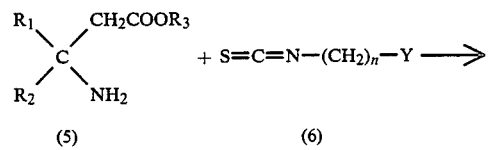

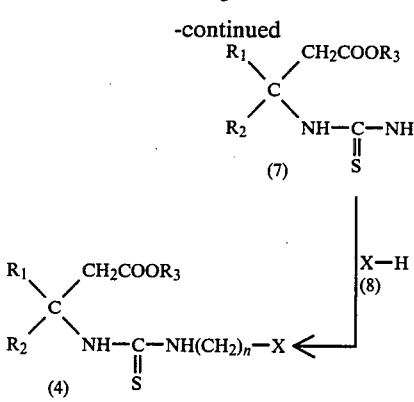

wherein $R_1$, $R_2$, $R_3$, X and n are as previously defined, and Y represents chlorine, bromine, iodine or a suitable leaving group, such as a tosylate or mesylate.

The compounds of formula (1) possess useful antianxiety properties. Anxiolytic properties are indicated using 5-HT$_{1A}$ in vitro receptor binding studies, see Middlemiss et al., Eur. J. Pharmacol., 90, 151-3 (1983) and Glaser et al., Arch. Pharmacol., 329, 211-215 (1985). Additionally, the anxiolytic properties for the compounds described herein can be demonstrated in vivo, utilizing a rat licking test, which is a recognized animal model for anxiety utilized by those skilled in the art, see Vogel et al., Psychopharmacologia, 21, 1-7 (1971).

In addition, the ω-[(2,3-dihydro-1,4-benzodioxin-2-yl)-methylamino] derivatives of formula (1a) possess antihypertensive properties. The antihypertensive effects of these compounds can be determined both in the anesthetized normotensive rat and/or in the conscious spontaneously hypertensive rat following the procedure of Fozard, J. Cardiovascular Pharm., 4, 829-838 (1982).

The compounds of this invention can be administered either orally, subcutaneously, intravenously, intramuscularly, intraperitoneally or rectally. The preferred route of administration is oral. The amount of compound to be administered can be any effective amount and will, of course, vary depending upon the patient, the mode of administration and the severity of the anxiety to be treated. Repetitive daily administration of the compounds may be desirable, and will vary depending upon the patient's condition and the mode of administration.

For oral administration, an anxiolytic or antihypertensive effective amount of compound can range from 0.005 to 10 mg/kg of patient body weight per day, preferably from 0.05 to 5 mg/kg of patient body weight per day. The preferred antianxiety dose of the compounds of formula (1a) is about 0.4 mg/kg of patient body weight per day. Pharmaceutical compositions in unit dose form contain from 1 to 50 mg of active ingredient and can be administered one or more times per day.

The compounds can be formulated into solid or liquid preparations such as capsules, pills, tablets, lozenges, melts, powders, solutions, suspensions or emulsions. Solid dosage unit forms generally employed include capsules or tablets. Capsules can be of the ordinary gelatin type which contain additional excipients such as, surfactants, lubricants and inert fillers such as lactose, sucrose and cornstarch. Tablets containing compounds of formula (1) can be formed with conventional tablet bases such as lactose, sucrose, and cornstarch in combination with binders, such as acacia, cornstarch or gelatin, disintegrating agents such as potato starch or alginic acid, and lubricants such as stearic acid or magnesium stearate.

For parenteral administration, an anxiolytic or antihypertensive effective amount of compound ranges from about 0.005 to 10 mg/kg of patient body weight per day, preferably from about 0.05 to 5 mg/kg of patient body weight per day. A parenteral composition in unit dose form contains from 0.1 mg to 10 mg of active ingredient and can be administered one or more times daily.

The compounds may be administered as injectable dosages of a solution or a suspension of the compound in a physiologically acceptable diluent with or without a pharmaceutical carrier. Suitable diluents or carriers include sterile liquids such as water or oils, with or without the addition of surfactants or other pharmaceutically acceptable adjuvants. Illustrative of various oils that can be employed in the practice of this invention are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solution.

The following examples illustrate the preparation of representative compounds employed in the practise of this invention, but are not intended to limit the invention in any way thereto.

EXAMPLE I

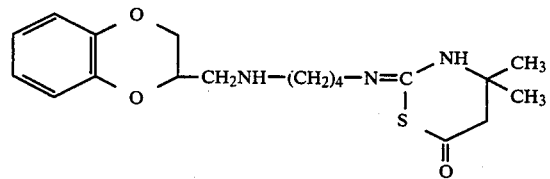

2-[4-[(2,3-dihydro-1,4-benzodioxin-2-yl)methylamino]butylimino]-tetrahydro-4,4-dimethyl-6H—1,3-thiazin-6-one oxalate N-Benzyl-(2,3-dihydro-1,4-benzodioxin-2-yl)methylamine A mixture of (2,3-dihydro-1,4-benzodioxin-2-yl)methylamine (4.13 g), benzaldehyde (2.65 g) and methylene chloride (25 ml) is stirred for 3 hours at room temperature and the methylene chloride removed via evaporation. A solution of the residue in ethanol (30 ml) is hydrogenated at atmospheric pressure and room temperature in the presence of methanesulphonic acid (2.4 g) and 10% palladium on charcoal (0.4 g). After the calculated quantity of hydrogen is consumed (510 ml), the solution is filtered, the ethanol is removed via evaporation, the residue is made alkaline with saturated aqueous potassium carbonate, and the resulting solution is extracted with ether. Evaporation of the dried ether extract yields an oily residue of N-benzyl-(2,3-dihydro-1,4-benzodioxin-2-yl)methylamine (5.9 g).

N-Benzyl-4-(2,3-dihydro-1,4-benzodioxin-2-yl)methylaminobutyronitrile

A mixture of N-benzyl-(2,3-dihydro-1,4-benzodioxin-2-yl)-methylamine (5.9 g), 4-chlorobutyronitrile (3.2 g) sodium carbonate (2.8 g) and isobutanol (30 ml) is refluxed for a period of 64 hours. The reaction mixture is concentrated to dryness under reduced pressure. The residue is partitioned in a mixture of ethyl acetate and water. The ethyl acetate fraction is purified using flash chromatography on a silica column using ethyl acetate-hexane (30:70) as eluant to yield N-benzyl-4-(2,3-dihydro-1,4-benzodioxin-2-yl)methylaminobutyronitrile as an oil (5.3 g).

N-(2,3-Dihydro-1,4-benzodioxin-2-ylmethyl)-1,4-diaminobutane

A solution of the above butyronitrile (5.3 g) in ethanol (50 ml) containing methanesulphonic acid (3.28 g) is hydrogenated at atmospheric pressure and room temperature, first in the presence of platinum oxide (Adams, 0.5 g) and then in the presence of 10% palladium on charcoal (0.5 g). After hydrogenation ceases (3 moles of $H_2$), the solution is filtered, concentrated, and the residue made strongly alkaline by the addition of aqueous sodium hydroxide. The product is extracted with methylene chloride and the solvent evaporated to yield N-(2,3-dihydro-1,4-benzodioxin-2-ylmethyl)-1,4-diaminobutane as an oil 2.55 g).

2-[4-[(2,3-dihydro-1,4-benzodioxin-2-yl)methylamino]butylimino]-tetrahydro-4,4-dimethyl-6H-1,3-thiazin-6-one oxalate A mixture of the above diamine (0.95 g), 2-ethoxycarbonyl 1,1-dimethylethylisothiocyanate (0.58 g), prepared as in Example II, and methylene chloride (5 ml) is refluxed for 2 hours. The solvent is evaporated, the residue is treated with ethereal oxalic acid and the precipitate is recrystallized from ethyl acetate to yield the desired 2-[4-[(2,3-dihydro-1,4-benzodioxin-2-yl)methylamino]butylimino]-tetrahydro-4,4-dimethyl-6H-1,3-thiazin-6-one oxalate, m.p. 210° C. (0.67 g).

EXAMPLE II

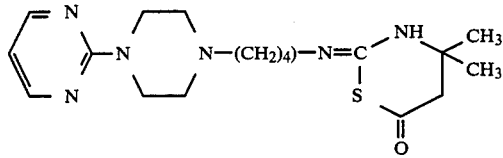

2-[4-[4-(2-Pyrimidinyl)-1-piperazinyl]butylimino]-tetrahydro-4,4-dimethyl-6H—1,3-thiazin-6-one Ethyl 2-Ethoxycarbonyl-1,1-dimethylisothiocyanate A solution of carbon disulphide (4.1 g) in methylene chloride (20 ml) is added to a stirred solution of ethyl 3-amino-3-methyl butyrate (7.8 g) in a mixture of triethylamine (5.5 g) and methylene chloride (30 ml) at −10° C. The mixture is stirred at room temperature for 15 minutes, cooled at 0° C., and treated with ethyl chloroformate (5.85 g). The temperature of the stirred mixture is allowed to rise to 20° C. for a period of 20 minutes and treated with a solution of triethylamine (5.5 g) in methylene chloride (30 ml). Stirring is continued for an additional 30 minutes. The mixture is washed with 5% NaOH solution, 5% HCl solution, water, dried and distilled. The compound, ethyl 2-ethoxycarbonyl-1,1-dimethylisothiocyanate, is collected at 80°–85° C./1 mm (5.2 g).

2-[4-[4-(2-Pyrimidinyl)-1-piperazinyl]butylimino]-tetrahydro4,4-dimethyl-6H-1,3-thiazin-6-one A mixture of ethyl 2-ethoxycarbonyl-1,1-dimethylisothiocyanate (1.87 g), 4[(2-pyrimidinyl)-1-piperazinyl]butylamine (2.45 g) and methylene chloride (10 ml) is refluxed for 2 hours. The solvent is removed by evaporation and the residue is recrystallized from ethyl acetate to yield the desired 2-[4-[4-(2-pyrimidinyl)-1-piperazinyl]butylimino]-tetrahydro-4,4-dimethyl-6H-1,3-thiazin-6-one, having a m.p. of 148° C. (3.1 g).

EXAMPLE III

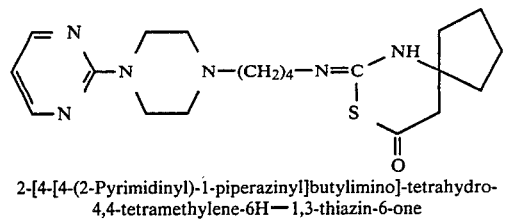

2-[4-[4-(2-Pyrimidinyl)-1-piperazinyl]butylimino]-tetrahydro-4,4-tetramethylene-6H—1,3-thiazin-6-one Cyclopentyl 1-Ethoxycarbonylmethylisocyanate Following essentially the same procedure as in Example II, utilizing ethyl 3-amino cyclopentyl acetate (15 g), carbon disulphide (6.9 g), triethylamine (2×8.86 g) and ethyl chloroformate (9.52 g), the desired cyclopentyl 1-ethoxycarbonylmethylisothiocyanate was obtained, which distilled at 102°–7° C./1 mm (2.8 g).

2-[4-[4-(2-Pyrimidinyl)-1-piperazinyl]butylimino]-tetrahydro-4,4-tetramethylene-6H,1,3-thiazin-6-one A mixture of 1-ethoxycarbonylmethyl cyclopentyl isothiocyanate (1.4 g), 4-(2-pyrimidinyl)-1-piperazinyl butylamine (1.61 g) and methylene chloride (10ml) is refluxed 2 hours. Potassium tert butoxide (0.1 g) is added and the stirred mixture is refluxed for an additional hour. After washing with water, the cooled methylene chloride solution is evaporated to dryness and the residue is recrystallized from ethyl acetate to yield the 2-[4-[4-(2-Pyrimidinyl)-1-piperazinyl]-butylimino]-tetrahydro-4,4-tetramethylene-6H-1,3-thiazin-6-one, having a m.p. of 128°–9° C. (2 g).

EXAMPLE IV

In vitro Determination of Anxiolytic Properties via 5-$HT_{1A}$ Binding

Radioligand binding studies of the 5-$HT_{1A}$ recognition sites are conducted in the following manner. Male normotensive Sprague-Dawley rat frontal cortex is dissected, frozen in liquid nitrogen and stored at −20° C. until needed. Tissues from 4–8 rats are pooled and homogenized in 70 vol Tris-HCl buffer (50 mM, pH 7.7), using a kinematica Polytron (setting 2/3 max speed, 20 sec). The homogenate is centrifuged (36500×g for 10 min), the pellet re-homogenised in the same volume of buffer and the process is repeated two more times. Between the second and third centrifugations the tissue homogenate is incubated at 37° C. for 10 min. The final pellet is suspended in the same volume of Tris buffer containing 10 M pargyline, 5.7 mM $CaCl_2$ and 0.1% ascorbic acid. This suspension is incubated for 10 min at 37° C. and then stored on ice until used in the binding assay.

Tissue homogenate (0.7 ml), radioactive ligand (0.1 ml) and the appropriate concentration of test compound (0.1 ml), together with buffer to a final volume of 1 ml are incubated at 37° C. for 15 min. Incubations are terminated by rapid filtration through Whatman GF/B filters followed by three 5 ml washes with ice-cold Tris-HCl buffer (50 mM, pH 7.0). Radioactivity is measured following extraction into Aquasol-Z (NEN) at an efficiency of 45–50%. The radioligand used to label the 5-$HT_{1A}$ recognition sites and its concentration is [3H]-8-hydroxy-2-(di-n-propylamino)-tetralin, [3H]-8-OH-DPAT, 1 mM.

Following essentially the above procedure, the following compounds were tested. Results are expressed as pIC$_{50}$ (log$_{10}$ concentration of test compound which inhibits specific binding by 50%).

| Test Compound | 5-HT$_{1A}$ Binding Affinity Rat Brain Cortex |
|---|---|
| Buspirone | 7.52 |
| Example I | 8.55 |
| Example II | 7.32 |
| Example III | 6.78 |

EXAMPLE V

In Vivo Determination of Anxiolytic Activity

Following the procedure described by Vogel et al., Psychopharmacologia 21, 1–7 (1971), thirsty naive rats are periodically administered shocks in an appropriate test apparatus for licking water, thereby setting up a simple conflict procedure. In the following experiment, naive adult male Sprague-Dawley rats (approximately 170 g) are randomly divided into 5 groups and deprived of water for 48 hours prior to the test session. Food is available in the home cage at all times.

Thirty minutes following subcutaneous injection, each animal is placed in the apparatus, permitted to find the drinking tube and complete 20 licks before shock is administered. The test animal controls shock duration by withdrawing from the drinking tube. At the termination of the first shock, shocks are delivered following each twentieth lick. The number of licks, indicating the number of shocks taken during a 3 minute period is recorded for each animal, compared with placebo, and with animals treated with established anxiolytic agents. A "release" from suppressed licking response, i.e., a greater number of licks compared to controls, is predictive of anxiolytic activity.

Following essentially this same procedure, the following results are observed utilizing the compound of Example II, i.e., 2-[4-[4-(2-pyrimidinyl)-1-piperazinyl]-butylimino]-tetrahydro-4,4-dimethyl-6H-1,3-thiazin-6-one

| Test Compound | Dose (mg/kg) | *Licks taken over 3 min. period |
|---|---|---|
| Control | — | 119 ± 30 |
| Diazepam | 0.75 | 247 ± 36 |
| Example II | 0.05 | 150 ± 28 |
|  | 0.25 | 223 ± 34 |
|  | 1.25 | 220 ± 27 |

*proportional to the number of shocks, inasmuch as each shock is equivalent to 20 licks.

We claim:

1. An aromatic ω-alkylamino-tetrahydro-6H-1,3-thiazin-6-one having the formula:

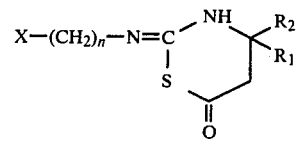

wherein n is an integer of from 2 to 5; R$_1$ and R$_2$ are each methyl or when taken together form a tetramethylene or a pentamethylene ring; X is the radical

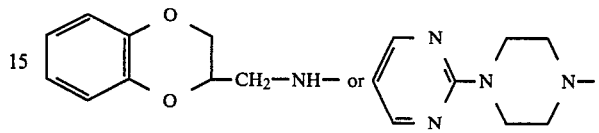

and the pharmaceutically acceptable acid addition salts thereof.

2. A compound according to claim 1 wherein X is the radical

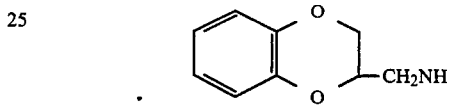

3. A compound according to claim 1, which is 2-[4-[(2,3-dihydro-1,4-benzodioxin-2-yl)methylamino]-butylimino]-tetrahydro-4,4-dimethyl-6H-1,3-thiazin-6-one.

4. A compound according to claim 1 wherein X is the radical

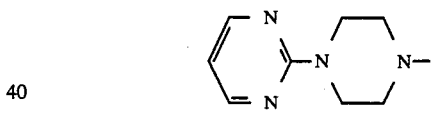

5. A compound according to claim 1, which is 2-[4-[4-(2-pyrimidinyl)-1-piperazinyl]butylimino]-tetrahydro-4,4-dimethyl-6H-1,3-thiazin-6-one.

6. A compound according to claim 1, which is 2-[4-[4-(2-pyrimidinyl)-1-piperazinyl]butylimino]-tetrahydro-4,4-tetramethylene-6H-1,3-thiazin-6-one.

7. A method for relieving the symptoms of anxiety in a patient in need thereof, which comprises the administration to said patient of an anxiolytic effective amount of a compound of claim 1.

8. An anxiolytic composition comprising an anxiolytic effective amount of a compound according to claim 1, or a pharmaceutically acceptable acid addition salt thereof, in combination with a pharmaceutically acceptable carrier or diluent.

* * * * *